United States Patent [19]

Kannankeril

[11] Patent Number: 5,372,877
[45] Date of Patent: Dec. 13, 1994

[54] BIODEGRADABLE CUSHIONING PRODUCT

[75] Inventor: Charles P. Kannankeril, North Caldwell, N.J.

[73] Assignee: Sealed Air, Saddle Brook, N.J.

[21] Appl. No.: 869,777

[22] Filed: Apr. 16, 1992

[51] Int. Cl.$^5$ .............................................. B32B 5/16
[52] U.S. Cl. ...................................... 428/283; 428/284; 428/288; 428/311.7; 428/317.9; 428/402; 428/903.3
[58] Field of Search ............ 428/283, 284, 288, 308.8, 428/311.1, 311.7, 326, 317.9, 402, 903.3; 162/168.1, 175

[56] References Cited

U.S. PATENT DOCUMENTS

| | | | |
|---|---|---|---|
| 3,852,224 | 12/1974 | Bridgeford | 260/2.5 M |
| 3,992,333 | 11/1976 | Emmons et al. | 260/2.5 R |
| 4,045,238 | 8/1977 | Battista et al. | 106/122 |
| 4,076,673 | 2/1978 | Burkholder, Jr. | 264/283 |
| 4,187,342 | 2/1980 | Holst et al. | 428/41 |
| 4,432,920 | 2/1984 | Ishikawa et al. | 264/49 |
| 4,508,595 | 4/1985 | Gasland | 162/158 |
| 4,612,332 | 9/1986 | Bock et al. | 521/65 |
| 4,857,065 | 8/1989 | Seal | 604/368 |

FOREIGN PATENT DOCUMENTS

| | | |
|---|---|---|
| 0255654 | 10/1988 | European Pat. Off. . |
| 9009529913 | 9/1088 | Japan . |
| WO90/11181 | 10/1990 | WIPO . |

*Primary Examiner*—James J. Bell
*Attorney, Agent, or Firm*—Bell, Seltzer, Park & Gibson

[57] ABSTRACT

This invention relates to a biodegradable foam product and composed of paper fibers or other cellulosic biodegradable material with a superabsorbent polymer and shaped into any desired shape and size and to processes for making same. The foam product is made by blending fibers with up to 25% by weight of a superabsorbent polymer, adding water to the blend allowing it to expand by letting the superabsorbent polymer soak up excess water and drawing off water. Upon drying, the foam product gives off water and the polymer shrinks to its original size leaving voids between the fibers while maintaining the expanded dimensions. The foam product is a soft material especially suited as a cushioning material.

12 Claims, 1 Drawing Sheet

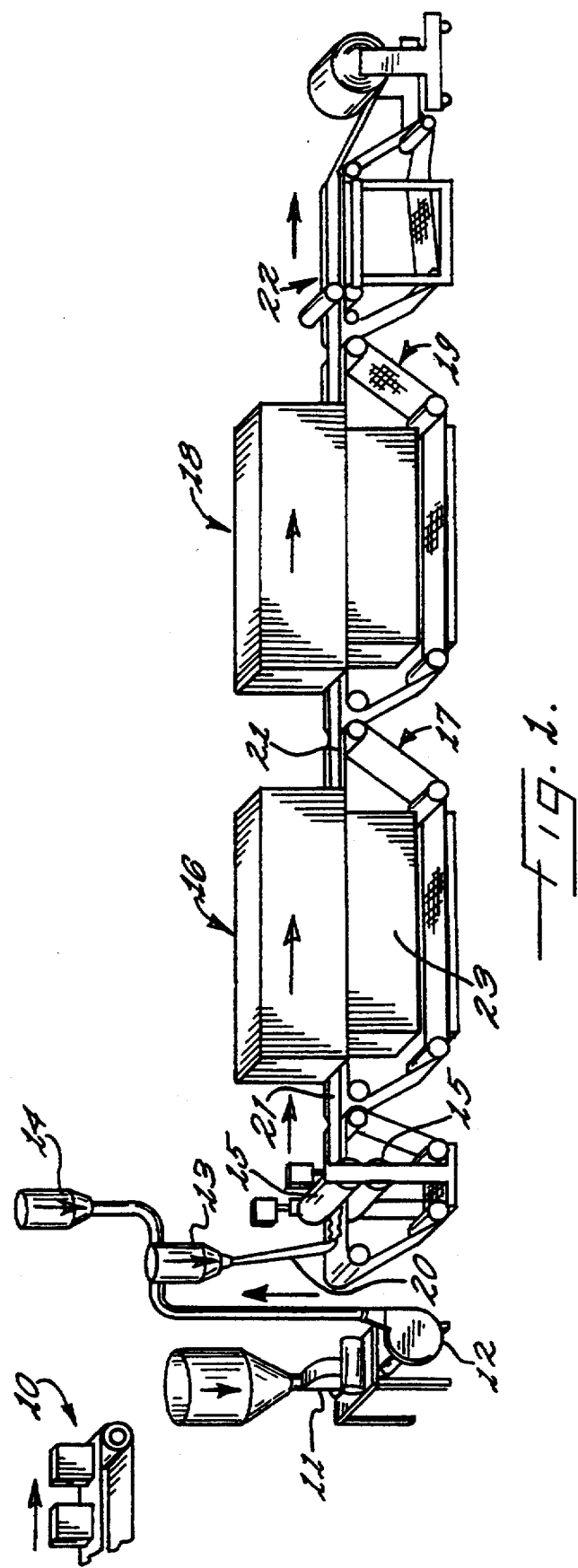

BIODEGRADABLE CUSHIONING PRODUCT

BACKGROUND OF THE INVENTION (1) Field of the Invention

This invention relates to a foamed product made by combining biodegradable cellulose fibers material and a superabsorbent polymer. More specifically, this invention relates to a foamed product made from cellulose fibers and a superabsorbent polymer, which is especially useful as a cushioning material, and to methods of making the foamed products.

(2) Description of the Prior Art

The prior art is replicate with products useful as cushioning or packaging material. These products are generally known as dunnage material. When shipping articles, especially fragile articles, it is desirable to make sure that the articles are safely packaged using dunnage material in one form or another. Dunnage materials include such things as bubble paper, styrofoam pellets, commonly known as "peanuts", ordinary tissue paper, embossed paper, foamed in place plastic materials and the like. While all of these dunnage materials provide a certain effectiveness as packaging materials, they are not universally suitable for every packing need.

Additionally, because disposal of waste paper in an increasing problem in our society, it is desirable to find beneficial uses for waste paper and certain other biodegradable fibrous materials. Reusable and biodegradable dunnage material provides a valuable use. Of course, there have been attempts to convert newsprint and other waste paper into useful products. Among the difficulties encountered in attempts to convert waste newsprint into useful products is newsprint's short length fibers and low potential strength.

There have also been disclosed numerous ways to form sheets of absorbent material from wood fibers and superabsorbent polymers. In such products, the wood fibers and the superabsorbent polymer are fixed in place mechanically and embossed to mechanically set in place the superabsorbent polymer. The thus formed product is used to absorb water or other liquid material. Such products have for years been converted into products to increase the absorbency such as diapers, sanitary napkins, absorbent cloths and pads, and the like. For example, one such product is disclosed in EPO Patent Application 255,654, wherein there is described an approach to making sheets of fibrous material in which cellulose fibers and superabsorbent polymers in the form of fibrils are formed into dry sheets. The fibers and superabsorbent polymer are suspended in an air stream of a mixture of fibers and polymer and dry formed onto one face of a moving permeable forming surface and hot calendaring or embossing to bind the materials.

Other approaches for combining cellulose fibers and superabsorbent polymers have been proposed. Some of these approaches use binders to attach the superabsorbent polymer and fibers together to make products useful for absorbing liquids. One such approach is set forth in PCT application WO 90/1181 which discloses coating fibers with at least about 7% by weight of one or more one or more liquid binders and applying a superabsorbent polymer to the fiber while the liquid binder on the fiber is still at least partially wet to uniformly adhere to the fibers.

The various products formed from combining cellulose fibers and superabsorbent polymers have been found useful as absorbent wipes or converted into other products but they have not been designed to meet the specific needs of the packaging industry.

SUMMARY OF THE INVENTION

In accordance with the present invention a biodegradable foam product is formed from cellulose fibers and a superabsorbent polymer. The product is made by mixing cellulose fibers or similar biodegradable material with a superabsorbent polymer and shaping it into a desire form. This product is allowed to expand by letting the superabsorbent polymers soak up water. Upon drying, the superabsorbent polymer gives off water and shrinks to its original size leaving voids between the fibers which maintains the expanded dimensions. The superabsorbent polymer also acts as a binder for the cellulose fibers. In another embodiment of this invention, the superabsorbent polymer and water are mixed and the polymer allowed to absorb the water prior to mixing with the fibers. Alternatively, the foam product may be made by forming a slurry of fiber and water, blending the superabsorbent polymer with the slurry and drying.

In accordance with a preferred method of this invention, cellulose fibers and up to about 25% by weight of said fibers of superabsorbent polymer, are blended in the absence of water to produce a blended mixture. Sheets are formed from the mixture by dry-laying wherein the blended mixture of cellulose fibers and superabsorbent polymer suspended in an air stream are laid onto the face of a moving porous web and calendared to the desired thickness or formed into some other desired shape. The sheets are wetted with sufficient water to allow the superabsorbent polymer to fully expand and then dried to drive off the water.

In another aspect of this invention, additional binding properties may be achieved by incorporating small amounts of latex adhesive in the water during the wetting process.

Thus, it is an object of this invention to provide a cushioning material which may be made from waste paper or other biodegradable fibrous material into a size and shape which is useful for packaging.

Another object of the present invention is to provide a biodegradable foamed product in which cellulose fibers and a superabsorbent polymer are formed together.

A further object of this invention is to provide a method of making a biodegradable foam product by blending fibers and superabsorbent polymer, forming a sheet or other shape of the fiber/polymer mixture, wetting the sheet to allow the superabsorbent polymer to swell and drying.

BRIEF DESCRIPTION OF THE DRAWINGS

Other objects, features and advantages of the invention will be readily understood from the following detailed description and drawing in which:

FIG. 1 is a flow sheet showing the various steps in the manufacture of the foam product of the present invention.

DETAILED DESCRIPTION OF THE PREFERRED EMBODIMENT

The foam products of the invention comprise making a product from fibers of biodegradable material and a superabsorbent polymer formed to any size and shape appropriate to its intended use. The foamed products are made from biodegradable fibrous material such as natural cellulose fibers, preferably from wood pulp. While any paper fibers may be used, the economically preferred end use of the products dictates the desirability for using waste or recycled paper, especially waste newsprint. It is not necessary to deink or bleach the paper. Preferred is waste newsprint which is commonly obtained in baled form and must be fiberized, for example, in a hammer mill, to be useful. Fiberizing the waste newsprint forms, for the most part, individual relatively short fibers generally about 25 mm. to 150 mm. long. The fiberized material may contain small amounts of fiber bundles but these fiber bundles are seldom detrimental to the final product.

Furthermore, it is not necessary that the foamed products of this invention be limited to recycle paper as any natural cellulose fibers may be used. Virgin wood pulp fibers from well-known pulping processes may also be used. Other natural cellulose fibers include a variety of materials such as bagrasse, hemp, jute, rice and corn stalks, cotton linters and the like. Also, other ground up, fiberized biodegradable material may be used, such as natural fibers, e.g., cotton linters.

The fiberized cellulose material is blended with a hydrophilic polymer, especially the so-called "superabsorbent" polymers. Superabsorbent polymers are synthetic cross-linked polymetric materials that are capable of absorbing many times their own weight of water or other liquids. Because superabsorbent polymers are significantly cross-linked, they are difficult to put into solution. Therefore, superabsorbent polymers are most commonly used as powders or granules.

The superabsorbent polymers suitable for application in the present invention are conventional superabsorbent polymers as that term is commonly applied in the art. Superabsorbent polymers are generally from one of three classes, namely starch graft copolymers, cross-linked carboxymethyl cellulose derivatives and modified hydrophilic polyacrylates. Examples of such materials are polymers of water soluble acrylic or vinyl monomers that are cross-linked with a polyfunctional reactant. Also included are starch modified polyacrylic acids and hydrolyzed polyacrylonitrile and their alkali metal salts. The acrylic polymers are preferred and are commercially available in particulate form mainly as polyacrylic acid.

A number of acrylic based superabsorbent polymers are commercially available and these are suitable for use in the present invention. A preferred commercially available superabsorbent polymer is Sanwet ®, a starch modified superabsorbent polymer available from Hoechst Celanese Corporation, Charlotte, N.C. Sanwet ® is a starch grafted polyacrylate sodium salt that has the capacity to absorb as much as 800 times its own weight in liquid. Other commercially available superabsorbent polymers include, for example, DRYTECH ® 520 superabsorbent polymer available from Dow Chemical Co., Midland, Mich. (Drytech ® is a superabsorbent derived from polypropenoic acid.); AQUA KEEP manufactured by Seitetsu Kagaku Co., Ltd.; ARASORB manufactured by Arakawa Chemical USA) Inc.; ARIDALL 1125 manufactured by Chemdall Corporation; and FAVOR manufactured by Stockhausen, Inc.

Among the superabsorbent polymers of the carboxymethyl cellulose derivative type are carboxymethyl cellulose or an alkaline metal salt thereof such as sodium carboxymethyl cellulose, hydroxy-ethyl cellulose, hydroxy-propylomethyl cellulose, methyl cellulose, regenerated cellulose derived from solutions of cellulose xanthate, carrageenan and collagen.

The blending may be accomplished using equipment well known in the art. It is important to make sure that the superabsorbent polymer are thoroughly distributed throughout the fibers to obtain a consistent product. Enough superabsorbent polymer is added to effectively form a foamed product when dried. The amount of superabsorbent polymer added is at least enough to effectively form the foamed product but it is not necessary to add more than 25% by weight. The upper limit of about 25% is a practical limit in that as the amount of superabsorbent polymer included in the foam product is increased about 25% the strength and density of the foam product decreases to the point where it is ineffective as a cushioning material. It is preferred that from about 5% to about 20% by weight of superabsorbent polymer be blended with the fibers. The higher the superabsorbent polymer loading, the less dense will be the resulting foam product.

It has been found that articles of a desired shape and size, e.g., a sheet, can be formed before adding water. The biodegradable foam product of the present invention can be dry-laid wherein the blended mixture of fibers and superabsorbent polymer is suspended in an air stream onto the face of a moving web and calendared to the desired thickness. Alternatively, water may be added directly to the superabsorbent polymer and the polymer allowed to swell before the fiber is blended with the swollen superabsorbent polymer. A rather thick gel is formed which may be extruded or cast into flat sheets of varying thickness for wrapping articles for cushioning protection or hollow tubes to be used as loose fill to cushion articles. The foamed products made by whichever process desired may be formed into specifically shaped members for supporting articles in place within a shipping container. Among such examples are corner posts and the like. Depending upon the article to be supported by, for instance, a corner post, the characteristics of the foam may be tailored to the specific need by adding to the product, where desirable, a latex adhesive. In an alternative embodiment of this invention, the foam product may be made by forming a slurry of fiber and water blending the superabsorbent polymer with the slurry and drying.

In a preferred embodiment, once the desired size and shape has been formed, water is added to the fiber/superabsorbent polymer blend in an amount sufficient to allow the superabsorbent polymer to swell to its desired extent. The superabsorbent polymer swells rapidly, in most circumstances in about a minute. The amount of swelling will determine the density of the final product. If a denser foamed product is desired either a small amount of superabsorbent polymer may be added or less water, which causes less swelling of the polymer and therefore less expansion of the foam.

The swollen article is fed to a drying oven where the heat drives off the water leaving voids between the cellulose fibers. The presence of the superabsorbent polymer also keeps the fibers bound together in one structure. The dried product will have an open cell foam structure and a density from about 1.0 to about 3.0 lbs/ft$^3$, preferably from about 1.5 to about 2.0 lbs/ft$^3$. The product is biodegradable and disintegrates easily in water.

In an alternative embodiment small amounts of a water soluble adhesive, such as a latex adhesive may be added to the water to form a stiffer product. It has been found that a latex binder of butadiene, acrylic or vinylacetate is particularly suitable. The latex may be added in amounts up to about 10% by weight, with about 5% by weight being preferred. As more than about 10% by weight latex is added, the foamed product begins to lose flexibility and therefore becomes undesirable as a cushioning material. Depending upon the amount of latex added to the water, the foamed article can be made from very soft and flexible to very hard and stiff.

While not of primary concern of cushioning material, the foamed product has a high liquid absorbing capacity. Despite having a high liquid absorbing capacity, the foam products of this invention are unsuitable for such uses because when used to absorb liquid, the foam products of the invention disintegrate into a gel-like mass. The high liquid absorption capacity of the final product can be minimized, if desired, by treating the product with sodium bicarbonate or similar salts to deactivate the superabsorbent polymer, in an amount of about 1% by weight.

In yet another embodiment, the foam product may be made with skins on one or both sides of the foam. In such embodiment, a sheet of thin dry-formed paper, Kraft paper or tissue paper is disposed under the air-laid intimate blend of fibers and superabsorbent polymer prior to adding water to form a composite sheet. The fiber/superabsorbent layer may also be covered by a second layer of thin dry-formed paper, Kraft paper, tissue paper, or the like.

Referring now to the drawings, there is shown in FIG. 1 a flow sheet of a preferred method for making the foam product of this invention. Cellulose material 10, preferably bales of waste paper, is fiberized in a suitable vessel such as a hydropulper, but preferably a hammermill 11, to separate the fibers. For most uses of the products of this invention, it is not necessary that the paper, if waste paper is used, be deinked. The paper fibers are conveyed via blower 12 to blender 13 where the fibers are intimately mixed with a superabsorbent polymer from feed 14.

From blender 13 the mixed fibers are moved to a formation zone which may be in line with the blender or may be separate equipment. The final product may be formed or shaped by extrusion from the blender into any desired form, such as sheets, tubes and the like. As shown in FIG. 1, the material 20 is air laid onto a moving permeable forming surface and formed into a sheet 21. The air-laid sheet is passed through calendar rolls 15 to compress the sheet to the desired thickness.

The sheet is passed on open-mesh conveyor 17, driven by rollers, through water feed station 16 While passing through water feed station 16, the sheet is sprayed with sufficient water to allow the superabsorbent polymer to swell to the desired extent. Excess water is collected and recovered from excess water box 23. The swollen sheet is then fed into drying oven 18 where the sheet is supported on open-mesh conveyor belt 19, driven by rollers, while the water is evaporated from the swollen fiber/superabsorbent sheet and the polymer shrinks to its original size, leaving voids in between the paper fibers. This process keeps the fibers bound together in one structure to form the foam product. The sheet of paper foam is passed through winder station 22 where it may be wound into a roll.

The following examples are provided to further illustrate various embodiments of the present invention. The examples are presented solely for purposes of illustration and are not to be construed as limiting the invention in any manner.

EXAMPLE 1

Compressed pulp board was fiberized in a hammer mill. The fiberized fluff was blended with 20% by weight of dry superabsorbent polymer fibrils, Stockhausen-Favor 900, a cross-linked polyacrylic salt using a desk top blender. The blended mixture was spread evenly on a 13 lb.wet strength tissue (approximately 6"×12") to form a mat. Another piece of wet strength tissue was placed on the top to cover the mat. These tissues need to be used only if an outer skin is desired on the final product.

Water was sprayed on the mat and the mat was allowed to expand as the superabsorbent polymer soaked up the water. The mat soaked up about 35–40 times the weight of the fluff mat in about 1 minute. Once the desired expansion was obtained, the swollen mat was dried in a conventional oven at 125° C. for 10 minutes. As the water evaporated, the superabsorbent polymer fibrils shrank to their original size, leaving voids between the fluff matrix. The resulting product was a flexible foam having a density of 1.5 lbs/ft$^3$. The product disintegrated when placed in water. The product was soft and provided excellent cushioning properties.

EXAMPLE 2

Compressed pulp board was fiberized in a hammer mill. Superabsorbent polymer particles (Favor 900 from Stockhausen) were mixed with water and allowed to swell. The swollen superabsorbent polymer [15% by weight] was blended with the fiberized fluff in a desk top blender to form a paste-like mixture. The resulting paste-like mixture was molded into a tube like configuration and dried. The resulting product was a foam article having a density of 1.8 lbs/ft$^3$ and was suitable as a cushioning material. It disintegrated when placed in water.

EXAMPLE 3

A foamed sheet was made according to the procedure used in Example 1 except that a 1% solution of latex (Elmer's white glue) was added to the fluff/SAP mixture instead of water. The resulting product had a density of 2.0 lbs/ft$^3$ and was somewhat stiffer than the product of Example 1.

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

What is claim is:

1. An expanded biodegradable fibrous product of self sustaining predetermined shape and adapted to be used as a low density cushioning material, said product comprising: an expanded mass of cellulose fibers arranged to form a porous reticulated structure, and a super absorbent polymer adhered to said expanded mass of cellulose fibers and bonding same to maintain the porous reticulated structure in a self-sustaining predetermined shape, said polymer having been swollen with water during formation of the product and subsequently dried, and said product having a density of from about 1.0 to about 3.0 lbs/ft$^3$.

2. The biodegradable fibrous product according to claim 1 wherein said product has a density of from about 1.5 to about 2.0 lbs/ft$^3$.

3. The biodegradable fibrous product according to claim 1 wherein said cellulose fibers are waste paper.

4. The biodegradable fibrous product according to claim 1 wherein said superabsorbent polymer is selected from the group consisting of starch graft copolymers, cross-linked carboxymethyl cellulose derivatives and modified hydrophilic polyacrylates.

5. The biodegradable fibrous product of claim 4 wherein said superabsorbent polymer is a sodium salt of a grafted starch polyacrylate.

6. The biodegradable fibrous product according to claim 1 wherein said product contains less than 25% by weight superabsorbent polymer.

7. The biodegradable fibrous product according to claim 6 wherein said product contains about 5% to about 18% by weight superabsorbent polymer.

8. The biodegradable fibrous product according to claim 1 further comprising up to about 10% by weight of a water soluble adhesive.

9. The biodegradable fibrous product according to claim 1 further comprising up to about 5% by weight of a latex adhesive.

10. A molded or shaped article formed of the product of claim 8.

11. The biodegradable fibrous product according to claim 1 wherein said product is a web and said web includes a paper layer on at least one side.

12. An expanded biodegradable fibrous cushioning material of self-sustaining predetermined shape and low density, said cushioning material consisting essentially of:

an expanded mass of waste newsprint fibers arranged to form a porous structure, from about 5% to about 18% by weight of a uniformly incorporated modified hydrophilic polyacrylate polymer distributed throughout and adhered to said expanded mass of fibers to maintain the porous fibrous cushioning material as an integral structure in a self-sustaining predetermined shape, from 0% to about 10% by weight of a water soluble adhesive, said polymer having been swollen with water during formation of the product and subsequently dried and having a density from about 1.0 to about 3.0 lbs/ft$^3$.

* * * * *